US007022750B2

(12) United States Patent
Camp et al.

(10) Patent No.: US 7,022,750 B2
(45) Date of Patent: Apr. 4, 2006

(54) ANTI-FOULING COATING CONTAINING COPPER AND GRAPHITE

(75) Inventors: Douglas R. Camp, Gibsonia, PA (US); Steven R. Zawacky, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 183 days.

(21) Appl. No.: 10/407,740

(22) Filed: Apr. 4, 2003

(65) Prior Publication Data

US 2004/0197322 A1 Oct. 7, 2004

(51) Int. Cl.
*C09D 5/16* (2006.01)
*C08K 3/04* (2006.01)
*C08K 3/22* (2006.01)

(52) U.S. Cl. ...................... 523/177; 523/122; 524/431; 524/495; 106/18.26

(58) Field of Classification Search ................ 523/122, 523/177; 428/78.09; 524/413, 495, 431; 106/18.26

See application file for complete search history.

(56) References Cited

U.S. PATENT DOCUMENTS 3,661,506 A * 5/1972 Watkins ......................... 422/6
4,197,233 A 4/1980 Marshall ................. 260/37 EP
4,286,988 A 9/1981 Castelli et al. ........... 106/15.05
4,323,599 A 4/1982 Marshall ..................... 427/181
4,428,989 A * 1/1984 Marshall .................... 428/35.8
4,835,050 A * 5/1989 Clayton ...................... 428/328
4,895,881 A 1/1990 Bigner ....................... 523/122
5,008,146 A 4/1991 Keohan ...................... 428/328
5,760,103 A 6/1998 Wentzell ..................... 523/122
5,773,508 A 6/1998 Tendo et al. ................ 524/549
5,976,229 A 11/1999 Ohmura et al. .......... 106/18.32
5,985,012 A * 11/1999 Nakamura et al. ....... 106/15.05
6,669,919 B1 * 12/2003 Greinke ...................... 423/448

FOREIGN PATENT DOCUMENTS

DE 2543698 A * 3/1977
EP 0 596 023 10/1998
JP 50087462 A * 7/1975
JP 60044568 A * 3/1985
JP 62142105 A * 6/1987

* cited by examiner

*Primary Examiner*—Tae H. Yoon
(74) *Attorney, Agent, or Firm*—Diane R. Meyers; Donald R. Palladino

(57) ABSTRACT

Anti-fouling compositions are disclosed. The compositions comprise a film-forming resin and effective amounts of graphite and copper. Methods for using the compositions are also disclosed, as are substrates coated with the compositions. The coatings find particular application on substrates that are submerged for extended periods of time in salt water. Methods for promoting oyster cultivation are also disclosed.

16 Claims, No Drawings

ANTI-FOULING COATING CONTAINING COPPER AND GRAPHITE

FIELD OF THE INVENTION

The present invention relates to compositions for reducing fouling of substrates that are in contact with water for extended periods of time. More specifically, the present invention relates to coating compositions containing effective amounts of graphite and copper and methods for using the same.

BACKGROUND OF THE INVENTION

The accumulation of biological growth on boat hulls, ship bottoms, ocean rigs, fish nets and other objects immersed in or at the level of sea water is a well-known problem. Biological growth that accumulates on the surface of these objects includes, for example, barnacles, mollusks, annelids, hydroids, algae, diatoms, hydrides, bryozoans, and protozoans. The accumulation of this growth leads to problems such as lowered running speeds due to increase in weight and stream resistance in the case of boats and ships, and a significantly shortened useful life in the case of fish nets, ocean rigs and other structures. In addition to the increase in the cost of fuel for boats and ships, there is also a loss associated in terms of both time and money in the application of remedial measures to the surfaces in contact with water.

One of the most common methods for preventing the accumulation of biological growth on substrates is by the use of anti-fouling paints. Such paints are applied to all surfaces of the substrate that will be exposed to water. Unfortunately, most anti-fouling paints do not prevent fouling for extended periods of time. In addition, many of the compositions used in anti-fouling paints are becoming environmentally unacceptable. For example, copper salts are used in many anti-fouling paints, as is tributyltin. Tributyltin, however, has been the subject of recent environmental restrictions; the use of large amounts of copper is raising environmental concerns as well.

Anti-fouling compositions that result in reduced release of copper to the environment are therefore desired.

SUMMARY OF THE INVENTION

The present invention provides coating compositions comprising a film forming resin, graphite and a source of copper. The graphite and copper are each present in amounts effective for inhibiting unwanted foulant growth on substrates. "Foulant" refers herein to both "hard" and "soft" fouling organisms. "Soft fouling organisms" generally refers to plants and invertebrates such as algae, kelp, bacteria, diatoms, hydrides, bryozoans, protozoans, soft corals, tunicates, hydroids, sponges, anemones and the like; the term "hard fouling organisms" refers generally to invertebrates having some type of hard outer shell, such as barnacles, tube worms, mollusks and the like. "Anti-fouling" refers to the inhibition of growth of any of these foulants; "fouling" as used herein also encompasses "sliming", which is the term generally used to describe the opaque film that forms on the surface of submerged objects, usually initiated by soft fouling organisms. Thus, the present compositions are useful for inhibiting fouling of substrates exposed to aquatic environments for extended periods of time. The present compositions are particularly useful in marine environments where exposure would be to salt water, although fresh water anti-fouling is also accomplished by the present invention.

As noted above, copper has long been used in coatings for its anti-fouling properties. It has been surprisingly discovered that use of graphite in conjunction with copper allows for a much lower amount of copper to be used, while still providing adequate if not improved protection against fouling. Thus, less copper is introduced to the environment.

DETAILED DESCRIPTION OF THE INVENTION

The present invention is directed to a coating composition comprising a film forming resin and effective amounts of both graphite and copper.

The present compositions can be formed from film-forming resins that are liquid, that is, water-borne or solvent-borne systems. Any resin that forms a film and that is suitable for use in a water environment can be used according to the present invention, absent compatibility problems. Examples of polymers useful in forming the resin include hydroxyl or carboxylic acid-containing acrylic copolymers, hydroxyl or carboxylic acid containing polyester polymers, oligomers and isocyanate or hydroxyl-containing polyurethane polymers, and amine or isocyanate-containing polyureas. These polymers are further described in U.S. Pat No. 5,939,491, column 7, line 7 to column 8, line 2; this patent, as well as the patents referenced therein, are incorporated by reference herein. Curing agents for these resins are also described in the '491 patent at column 6, lines 6–62. Combinations of curing agents can be used.

In a particularly suitable embodiment, the film forming resins are amine resins, epoxy resins or mixtures thereof. Such resins include EPON 880 and EPON 1001 epoxy resins, available from Resolution Performance Products and DEN 444 from Dow Chemical. Amine resins include VERSAMINE 115, VERSAMIDE 125 and VERSAMIDE 140 from Henkel. Other suitable amines are described in U.S. Pat. No. 4,428,989, column 5, line 62 to column 6, line 38 and other suitable epoxides are described in the same patent at column 4, line 18 to column 5, line 60.

The film forming resin is generally present in the coating compositions in an amount greater than about 10 weight percent, such as greater than about 20 weight percent, and less than 98 weight percent, with weight percent being based on the total active component weight of the composition. "Active component weight" means the combined weight of the resin, curing agent if used, the graphite, the copper, and any additives; that is, the weight of all the components except the solvent. For example, the weight percent of resin can be between 30 and 60 weight percent. When a curing agent is used, it is generally present in an amount of up to 50 weight percent; this weight percent is again based on the total active component weight of the composition.

Solvents in which the present coatings may be dispersed include, for example, water, alcohols, ketones, aromatic hydrocarbons, glycol ethers, esters or mixtures thereof. The solvent is generally present in amounts ranging from 5 to 80 weight percent based on total weight of the composition, such as 15 to 50 weight percent.

The present compositions also comprise an effective amount of graphite. Graphite is commercially available in many forms. Particularly suitable for the present invention is graphite in granular or flake form, such as graphite having a particle size of from 0.1 to 500 microns. Such a product is commercially available from Lonza Ltd. as LONZA KS44. A particularly suitable graphite is expandable graphite. Expandable graphite is graphite that has been intercalated with one or more inorganic acids. Expandable graphite is commercially available from Chuetsu Corporation, Japan, Beijing Advanced Materials Co., Asbury Graphite Mills, Superior Graphite Co., UCAR Carbon Company, NGS and Hebei Maoyuan.

The compositions of the present invention further comprise an effective amount of copper. Copper can be introduced in many forms. For example, metallic copper, such as in particle or flake form, can be used. Alternatively, copper can be introduced in any other form such as copper oxide, copper (I) thiocyanate, copper naphthenate, copper octoate, copper rosinate, copper ethylene bisporene dithiocarbamate, copper carbonate, copper (II) chromate, copper (II) citrate, copper (II) ferrocyanate, copper (II) fluoride, copper (II) hydroxide, copper (II) quinoline, copper-∝-hydroquinoline, copper (II) oleinate, copper (II) oleate, copper (II) nitrate, copper (II) oxalate, copper (II) phosphate, copper (II) stearate, copper (II) sulfide, copper (II) tartrate, copper (II) tungstate, copper (I) bromide, copper (I) iodide, copper (I) rhodanide, copper (I) sulfide, and copper (II) sulfite. Copper (I) oxide ("cuprous oxide") is a particularly suitable form by which to introduce the copper.

As noted above, effective amounts of both graphite and copper are used in the present invention. The term "effective amount" in reference to the graphite and copper refers to that amount of graphite and that amount of copper which, together, will impart anti-fouling properties to the present compositions. "Anti-fouling" as noted above refers to the inhibition of unwanted growth of the hard and/or soft fouling organisms discussed above. Any inhibition of fouling (which again includes sliming) is "anti-fouling" according to the present invention. Typically, the graphite and copper together will be present in an amount of at least about 10 weight percent, such as at least about 20 weight percent, with weight percent being based on the total active component weight of the composition. The graphite and copper can be used in approximately equal amounts; it will be appreciated that because approximately half of the copper normally needed to effect anti-fouling can be replaced with graphite in certain embodiment of the present compositions, the amount of copper used in the compositions is significantly reduced as compared with other copper-containing anti-fouling coatings. This is a significant advantage of the present invention in that environmental exposure to copper is minimized.

The compositions of the present invention can further contain conventional additives, such as plasticizers, antioxidants, light stabilizers, UV absorbers, thixotropic agents, anti-gassing agents, organic co-solvents, other biocides, antibiotics, pesticides, herbicides, surfactants, flow-control additives and catalysts. Any such additives known in the art can be used, absent compatibility problems. Such additives, if used, will typically comprise less than 20 weight percent of the composition, with weight percent being based on total weight of the composition. In one particular embodiment, the present compositions specifically exclude fluorocarbon-containing polymers, and in another embodiment zinc is specifically excluded.

Any of various organic or inorganic pigments can also be included in the present compositions. Examples include titanium dioxide, talc, barium sulfate, silica, iron oxide, mica, clay, aluminum oxide, calcium carbonate, carbon black, phthalocyanine blue and phthalocyanine green.

The present invention is further directed to a method for inhibiting fouling on a submerged substrate comprising applying to the substrate any of the anti-fouling compositions described above. The compositions can be applied by any conventional method such as brushing, dipping, flow coating, roll coating, conventional and electrostatic spraying. Typically, dry film thickness for the present coatings can range between 1 and 15 mils, such as between 2 and 10 mils or about 6 mils.

The present invention is further directed to substrates coated with any of the compositions described above. Suitable substrates can be made from any material subject to fouling including metallic and non-metallic substrates such as fiber glass and the like. The substrates can be moving (such as boats or ships) or fixed structures, including structures that are used in the processing of bulk water. Substrates treated according to the present invention will generally be those that are at, near or beneath the water's surface for extended periods of time, i.e. greater than about four months ("submerged substrate").

It has been surprisingly discovered that while the present compositions inhibit growth of unwanted foulants, they do not inhibit growth of oysters. Growth of oysters on substrates treated according to the present invention may be observed, for example, about ten months after treatment. This result was surprising since growth of virtually every other hard and soft fouling organism is inhibited. Accordingly, the present invention is further directed to a method for promoting oyster cultivation comprising applying to a substrate any of the compositions described above. The compositions can be applied in the manner described above.

As used herein, unless otherwise specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa. Also, as used herein, the term "polymer" is meant to refer to oligomers and both homopolymers and copolymers; the prefix "poly" refers to two or more.

EXAMPLES

The following examples are intended to illustrate the invention, and should not be construed as limiting the invention in any way.

Example 1

Liquid coatings were prepared from ingredients in the amounts shown (in grams) in Table 1.

TABLE 1

| | Samples | | | | | | | | | |
|---|---|---|---|---|---|---|---|---|---|---|
| | Sample 1* | | Sample 2* | | Sample 3 | | Sample 4 | | Sample 5 | |
| | Wt. | % Act. | Wt. | % Act. | Wt. | % Act. | Wt. | % Act. | Wt. | % Act. |
| Epoxy coating[1] | — | — | — | — | — | — | — | — | — | — |
| Dispersing additive[2] | 2.09 | 1.4% | 2.09 | 1.5% | 4.88 | 4.1% | 5.42 | 4.6% | — | — |
| Vinyl solution[3] | 6.35 | 2.0% | 6.35 | 2.2% | 14.83 | 6.1% | 16.48 | 6.9% | — | — |
| Triethylene-tetramine[4] | 0.94 | 1.4% | 0.94 | 1.5% | 2.19 | 4.1% | 2.44 | 4.6% | — | — |
| MIBK/xylene mixture[5] | 9.05 | — | 9.05 | — | 21.13 | — | 23.49 | — | — | — |
| Tricresyl phoshate[6] | 2.50 | 3.6% | 2.50 | 3.9% | 5.84 | 10.8% | 6.49 | 12.2% | — | — |
| Gum rosin solution[7] | 13.59 | 7.0% | 13.59 | 7.6% | 31.73 | 21.1% | 35.28 | 23.9% | — | — |
| Epoxy resin[8] | — | — | — | — | — | — | — | — | 13.14 | 24.5% |
| Geraniol[9] | — | — | — | — | — | — | — | — | — | — |
| Molybdenum sulfide[10] | — | — | — | — | 5.69 | 10.5% | 5.42 | 10.2% | — | — |
| Zinc omadine[11] | 4.88 | 7.1% | — | — | 3.06 | 5.7% | — | — | 3.74 | 7.0% |
| Expandable graphite[12] | — | — | — | — | 11.39 | 21.1% | 10.82 | 20.4% | — | — |
| Cuprous oxide[13] | 52.26 | 75.5% | 52.26 | 81.2% | 5.69 | 10.5% | 5.42 | 10.2% | 14.25 | 26.6% |
| Amine curative[14] | — | — | — | — | — | — | — | — | 28.86 | 42.0% |
| MIBK/xylene mixture[15] | 1.74 | — | 1.74 | — | 4.06 | — | 4.52 | — | — | — |
| Vinyl solution | 6.35 | 2.0% | 6.35 | 2.2% | 14.83 | 6.1% | 16.48 | 6.9% | — | — |
| Xylene | — | — | — | — | — | — | — | — | 7.20 | — |
| Totals | 99.75 | 100.0% | 94.87 | 100.0% | 125.32 | 100.0% | 132.26 | 100.0% | 67.19 | 100.0% |

| | Samples | | | | | | | | | |
|---|---|---|---|---|---|---|---|---|---|---|
| | Sample 6 | | Sample 7 | | Sample 8 | | Sample 9 | | Sample 10 | |
| | Wt. | % Act. | Wt. | % Act. | Wt. | % Act. | Wt. | % Act. | Wt. | % Act. |
| Epoxy coating[1] | — | — | — | — | — | — | — | — | 25.00 | 31.5% |
| Dispersing additive[2] | — | — | — | — | — | — | — | — | — | — |
| Vinyl solution[3] | — | — | — | — | — | — | — | — | — | — |
| Triethylene-tetramine[4] | — | — | — | — | — | — | — | — | — | — |
| MIBK/xylene mixture[5] | — | — | — | — | — | — | — | — | — | — |
| Tricresyl phoshate[6] | — | — | — | — | — | — | — | — | — | — |
| Gum rosin solution[7] | — | — | — | — | — | — | — | — | — | — |
| Epoxy resin[8] | 13.14 | 26.3% | 10.88 | 15.1% | 10.88 | 17.7% | 11.97 | 26.3% | — | — |
| Geraniol[9] | — | — | — | — | — | — | 2.17 | 4.8% | — | — |
| Molybdenum sulfide[10] | — | — | 9.35 | 13.0% | 7.99 | 13.0% | 10.81 | 23.8% | — | — |
| Zinc omadine[11] | — | — | 5.04 | 7.0% | — | — | — | — | — | — |
| Expandable graphite[12] | — | — | 18.71 | 26.0% | 15.98 | 26.0% | — | — | 15.93 | 23.7% |
| Cuprous oxide[13] | 14.25 | 28.6% | 9.35 | 13.0% | 7.99 | 13.0% | — | — | 10.62 | 15.8% |
| Amine curative[14] | 28.86 | 45.1% | 23.90 | 25.9% | 23.90 | 30.3% | 26.29 | 45.1% | 25.00 | 29.0% |
| MIBK/xylene mixture[15] | — | — | — | — | — | — | — | — | — | — |
| Vinyl solution | — | — | — | — | — | — | — | — | — | — |
| Xylene | 6.50 | — | 21.60 | — | 8.50 | — | 3.50 | — | — | — |
| Totals | 62.75 | 100.0% | 98.83 | 100.0% | 75.24 | 100.0% | 54.74 | 100.0% | 76.55 | 100.0% |

*Samples 1 and 2 are comparative formulations based on those published by Arch Chemicals "Zinc Omadine Bactericide-Fungicide for Antifouling Marine Paint".
[1]Obtained from PPG Industries, Inc. as PITT-GUARD 97-946.
[2]Obtained from BYK-Chemie as DISPERBYK 163.
[3]Vinyl resin obtained from Union Carbide as VYHH; solution was 22.2% vinyl resin in MIBK/Xylene solvent.
[4]Obtained from Dow Chemical.
[5]Samples 1 and 2, MIBK = 5.43 g, xylene = 3.62 g
Sample 3, MIBK = 12.68 g, xylene = 8.45 g
Sample 4, MIBK = 14.0 g, xylene = 9.4 g
[6]Obtained from Fisher Scientific.
[7]Gum rosin obtained from Akzo Nobel; solution was 35.9% gum rosin in MIBK/xylene solvent.
[8]Obtained from Resolution Performance Products as EPON 880.
[9]Terpene alcohol obtained from Fisher Scientific.
[10]Obtained from Fisher Scientific.
[11]Obtained from Arch Chemicals.
[12]Obtained from Asbury Graphite Mills, Inc. as grade 3538.
[13]Obtained from American Chemet as Lolo TINT 97.
[14]Obtained from PPG Industries, Inc. as PITT-GUARD 97-949.
[15]Samples 1 and 2, MIBK = 1.04 g, xylene = 0.70 g
Sample 3, MIBK = 2.43 g, xylene = 1.63 g
Sample 4, MIBK = 2.70 g, xylene = 1.81 g One-quarter inch thick steel panels were coated with Samples 1–10 prepared as described above. Samples were applied by air atomized hand spray and allowed to dry before shipment to the test site. The coatings on all the panels had a dry film thickness of 3.25 to 6.0 mils. The coated panels were then submerged in salt water at Ponce Inlet, Florida. The panels were checked every month for foulant growth. A control panel of uncoated plastic was also tested. The control panel was scraped free of foulant growth when fouling was severe. Thus, foulant growth for the control panel as discussed below represented one month's worth of growth in Table 2. A blank rating in the tables indicates that there was none of that particular fouling on the panels. All measurements shown under the sub-heading "size" are in millimeters, and "%" refers to the percent of the area on the panel that was affected.

Growth was rated on a scale of 0–10, 10=clean or no fouling and 0=complete failure.

Tr(s)=trace(s) of foulant growth.

"S" stands for seed barnacle, which is the stage of a barnacle right after it settles onto a surface. The size of a barnacle during the seed stage is less than 1 mm. Thus, the description "S-8" means that a panel had barnacles ranging in size from seed to 8 mm.

"P" stands for pinpoint, used to describe the youngest stage of an annelid tube formation, which normally is circular in shape and about 1 mm in diameter.

TABLE 2

| PANEL NO. | GEN PERF | BARNACLES ** Rating | BARNACLES ** Size | MOLLUSKS Rating | MOLLUSKS Size | ANNELIDS Rating | ANNELIDS Size | HYDROIDS Rating | HYDROIDS % | BRYOZOA ENCRUSTING Rating | BRYOZOA ENCRUSTING % | BRYOZOA FILAMENTOUS Rating | BRYOZOA FILAMENTOUS % | ALGAE Filamentous % | SCUM & Silt |
|---|---|---|---|---|---|---|---|---|---|---|---|---|---|---|---|
| 1 | 10 | — | — | — | — | — | — | Tr | 1 | — | — | — | — | — | 8 |
| 2 | 10– | — | — | — | — | — | — | 5 | 50 | — | — | — | — | Trs | 4 |
| 3 | 10– | Trs | S-10 | — | — | Trs | P-10 | Trs | 4 | Tr | 1 | Trs | 2 | — | 6 |
| 4* | 9 | 10 | S-3 | — | — | 10 | P-18 | Tr | 1 | Trs | 2 | Tr | 1 | Tr | 6 |
| 5 | — | Panel obscured by fouling | | | — | — | — | — | — | — | — | — | — | — | — |
| 6 | — | Panel obscured by fouling | | | — | — | — | — | — | — | — | — | — | — | — |
| 7 | — | Panel obscured by fouling | | | — | — | — | — | — | — | — | — | — | — | — |
| 8 | 9 | 10– | S-10 | — | — | Tr | P-15 | 9 | 10 | 9 | 10 | — | — | Tr | 6 |
| 9 | — | Panel obscured by fouling | | | — | — | — | — | — | — | — | — | — | — | — |
| 10 | 9 | 10– | S-8 | — | — | Trs | P-30 | 7 | 30 | — | — | — | — | 10 | 6 |
| Control | 0 | Panel heavily fouled mainly barnacles | | | | | | | | | | | | | |

*Blisters noticed on Panel 4 when rack was pulled for initial photos. Only fouling on topcoat was rated.
** Some barnacles are undercutting coating.

For the readings provided in Table 2:

1) At time of inspection all panels were sprayed with street-pressure fresh water, then kept wet with salt water.
2) Scum and silt ratings were performed before the water rinse.
3) Panel edges and mounting holes were not considered during the ratings.

As demonstrated in Table 2, at ten months several compositions of the present invention gave results comparable to those of panels 1 and 2, which used very high percentages of cuprous oxide, with or without zinc omadine. The control panel with no coating was completely fouled.

Whereas particular embodiments of this invention have been described above for purposes of illustration, it will be evident to those skilled in the art that numerous variations of the details of the present invention may be made without departing from the invention as defined in the appended claims.

It is claimed:

1. A coating composition comprising a liquid solvent, a film forming resin and effective amounts of graphite and copper, wherein the coating composition does not include an organotin containing material.

2. The coating composition of claim 1, wherein the graphite is in flake or granular form.

3. The coating composition of claim 1, wherein the graphite is expandable graphite.

4. The coating composition of claim 1, wherein the copper is in the form of cuprous oxide.

5. The coating composition of claim 4, wherein the graphite is expandable graphite.

6. The coating composition of claim 1, wherein the film forming resin is an epoxy amine resin.

7. The coating composition of claim 1, wherein the film forming resin is present in a weight percent of 1 to 98; the graphite is present in a weight percent of 1 to 50; and the copper is present in a weight percent of 1 to 50, with weight percent being based on the total active component weight of the composition.

8. A method for inhibiting fouling on a submerged substrate comprising applying to said substrate the coating of claim 1.

9. A substrate to which has been applied the coating of claim 1.

10. A coating composition comprising a liquid solvent, a film forming resin and effective amounts of expandable graphite and copper, wherein the coating composition does not include a triorganotin containing material.

11. The coating composition of claim 10, wherein the graphite is in flake or granular form.

12. The coating composition of claim 10, wherein the copper is in the form of cuprous oxide.

13. The coating composition of claim 10, wherein the film forming resin is an epoxy amine resin.

14. The coating composition of claim 10, wherein the film forming resin is present in a weight percent of 1 to 98; the expandable graphite is present in a weight percent of 1 to 50; and the copper is present in a weight percent of 1 to 50, with weight percent being based on the total active component weight of the composition.

15. A method for inhibiting fouling on a submerged substrate comprising applying to said substrate the coating of claim 10.

16. A substrate to which has been applied the coating of claim 10.

* * * * *